US00PP17259P2

(12) United States Plant Patent
Schoenmakers

(10) Patent No.: US PP17,259 P2
(45) Date of Patent: Dec. 5, 2006

(54) *FITTONIA* PLANT NAMED 'WHITE STAR'

(50) Latin Name: *Fittonia verschaffeltii*
Varietal Denomination: White Star

(75) Inventor: Kees Schoenmakers, Haaren (NL)

(73) Assignee: Schoenmakers Tropische Potcultures, Haaren (NL)

( * ) Notice: Subject to any disclaimer, the term of this patent is extended or adjusted under 35 U.S.C. 154(b) by 4 days.

(21) Appl. No.: 11/172,361

(22) Filed: Jun. 30, 2005

(51) Int. Cl.
*A01H 5/00* (2006.01)

(52) U.S. Cl. ..... Plt./373
(58) Field of Classification Search ..... Plt./373
See application file for complete search history.

(56) References Cited

U.S. PATENT DOCUMENTS

PP4,516 P * 4/1980 Engelmann ..... Plt./373
PP4,602 P * 10/1980 Cobia ..... Plt./373

OTHER PUBLICATIONS

UPOV ROM GTITM Computer Database, GTI Jouve Retrieval Software 2005/05 Citations for 'White Star'.*

* cited by examiner

*Primary Examiner*—Wendy Haas

(57) ABSTRACT

A new cultivar of *Fittonia* plant named 'White Star' that is characterized by small light green to white leaves with dark green margins.

1 Drawing Sheet

Botanical classification: *Fittonia verschaffeltii.*
Variety denomination: 'White Star'.

BACKGROUND OF THE INVENTION

The present invention relates to a new and distinct cultivar of *Fittonia* plant botanically known as *Fittonia verschaffeltii* and hereinafter referred to by the cultivar name 'White Star'.

The new cultivar was discovered by the inventor in a cultivated area of Haaren, The Netherlands in 2003. 'White Star' was discovered as a naturally occurring whole plant mutation of *Fittonia verschaffeltii* 'White Anne' (not patented).

Asexual reproduction by terminal cuttings of the new cultivar 'White Star' was first done in 2003 in Haaren, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Fittonia* cultivar 'White Star'.

1. *Fittonia* 'White Star' exhibits small leaves.
2. *Fittonia* 'White Star' exhibits light green to white leaves with dark green margins.

The closest comparison cultivars are *Fittonia* 'White Anne' (unpatented) and *Fittonia* 'Pink Star' (unpatented). The new cultivar 'White Star' is distinguishable from the parent plant 'White Anne' by the following characteristics:

1. 'White Star' has a more compact habit.
2. 'White Star' has crenate leaf margins.

The new cultivar 'White Star' is distinguishable from 'Pink Star' by the following characteristics:

1. 'White Star' has a white veins. 'Pink Star' has pink veins.

BRIEF DESCRIPTION OF THE DRAWING

The accompanying photograph illustrates the distinguishing traits of *Fittonia* 'White Star'. The plant in the photograph shows an overall view of a 12 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Fittonia* cultivar named 'White Star'. Data was collected in Haaren, The Netherlands from 12 week old greenhouse grown plants in 8.5 cm. containers. The time of year was Spring and the average temperature was 24 degrees Centigrade during the day and 22 degrees Centigrade at night. No photoperiodic treatments were used. Color determinations are in accordance with The Royal Horticultural Society Colour Chart 2001 edition, except where general color terms of ordinary dictionary significance are used. The growing requirements are similar to the species. 'White Star' has not been tested under all possible conditions and phenotypic differences may be observed with variations in environmental, climatic, and cultural conditions, however, without any variance in genotype.

Botanical classification: *Fittonia verschaffeltii* 'White Star'.
Use: Ornamental.
Parentage: 'White Star' is a naturally occurring whole plant mutation of *Fittonia* 'White Anne'.
Vigor: Moderate.
Growth rate: Moderate.
Growth habit: Broad spreading, upright.
Plant shape: Flattened globular.
Suitable container size: 8.5 cm. diameter container.
Height: Average 4.4 cm.

Width: Average 8.9 cm.
Hardiness: USDA Zone 10.
Propagation: Terminal cuttings.
Time to initiate roots: Approximately 21 days to produce roots on an initial cutting at 24 degrees Centigrade.
Time to produce a rooted cutting: Approximately 35 days to produce a rooted cutting at 24 degrees Centigrade.
Crop time: 12 weeks.
Root system: Fine and fibrous.
Stem:
*Branching habit.*—Moderately branching.
*Average number of lateral branches.*—2.
*Pinching.*—Not needed.
*Lateral branch diameter.*—3 mm. in diameter.
*Lateral branch length.*—3.2 cm. in length.
*Lateral branch strength.*—Moderate.
*Stem color.*—138B.
*Pubescence.*—Dense, length 1 mm, color N155A.
*Internode length.*—8 mm. between nodes.
*Internode color.*—144B.
*Shape.*—Rounded, dull.
*Surface.*—Dull.
*Stem strength.*—Moderate.
Foliage:
*Leaf arrangement.*—Opposite.
*Compound or single.*—Single.
*Leaf shape.*—Oblanceolate to broad obovate, slightly convexed.
*Leaf apex.*—Acute.
*Leaf base.*—Attenuate.
*Leaf texture.*—Dull, rugose.
*Leaf length.*—Average 4.5 cm. in length.
*Leaf width.*—2 mm. in width.
*Quantity of leaves per lateral branch.*—Average 8.
*Pubescence.*—Short hairs on margins, 0.5 mm. in length, N155A.
*Leaf margin.*—Repand and considerably wavy.
*Vein pattern.*—Pinnate.
*Young leaf color,* (*upper surface*).—145D with spots 145A to 145B, margins colored 137A to 139A.
*Young leaf color,* (*lower surface*).—144B to 144C, venation colored 145D, margins colored 137A to 139A.
*Mature leaf color,* (*upper surface*).—191C to 192C, margins colored 139A.
*Mature leaf color,* (*lower surface*).—Between 137C to 138A, margins colored between 137A and 139A.
*Vein color* (*upper surface*).—Between 155C to 157A.
*Vein color* (*lower surface*).—145B to 145C.
*Leaf attachment.*—Petiolate.
*Petiole dimensions.*—Average 1.4 cm. in length, 2.2 mm. in diameter, 1.5 mm. in height.
*Petiole color.*—144B.
*Durability of foliage to stress.*—High.
Flowers: Flowers have not been observed.
Disease and insect resistance: Plants of the new *Fittonia* have not been observed for disease or insect resistance.

It is claimed:

1. A new and distinct variety of *Fittonia* plant named 'White Star' as described and illustrated.

* * * * *

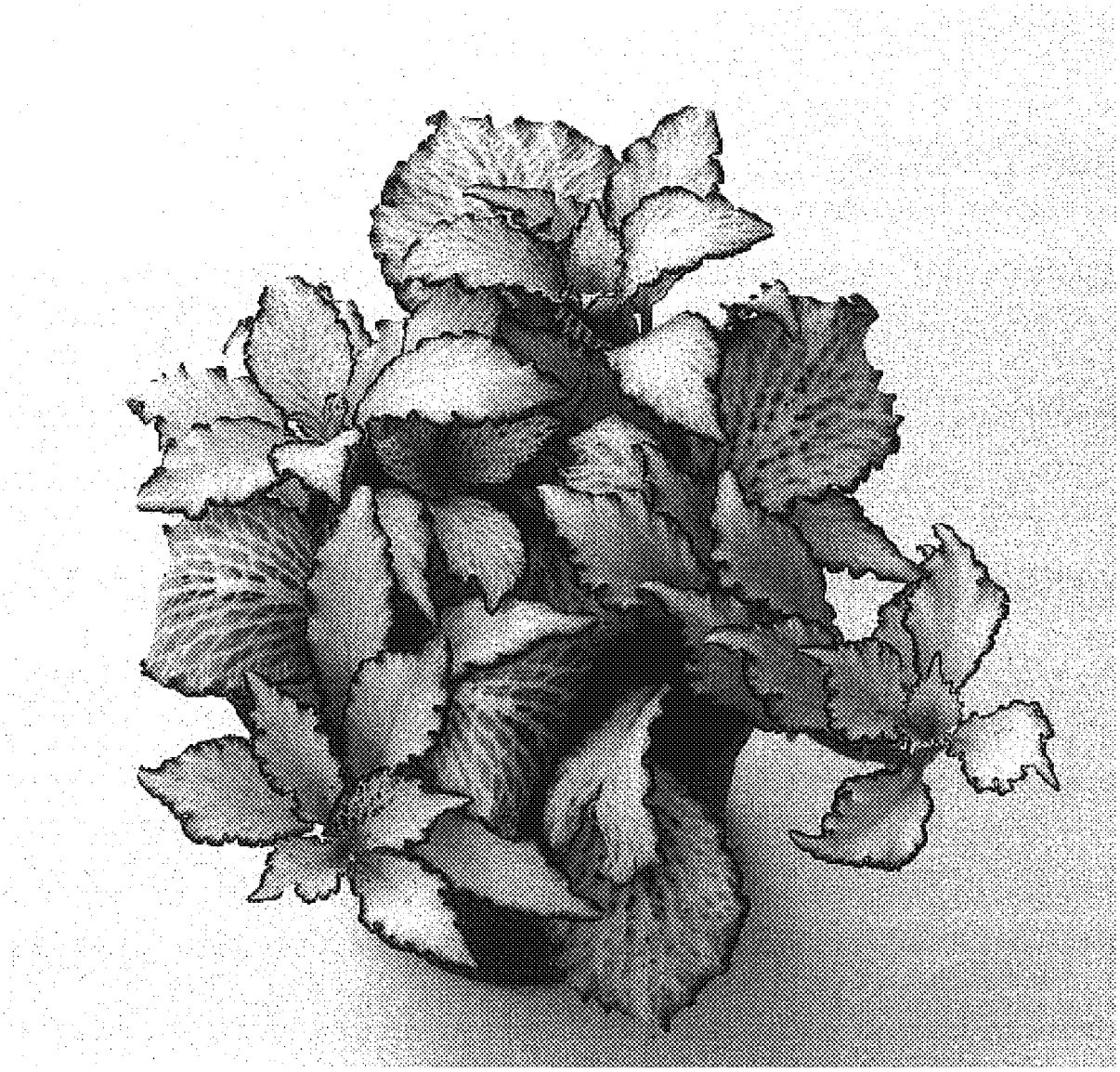
1